United States Patent [19]
Baker et al.

[11] Patent Number: 5,446,925
[45] Date of Patent: Sep. 5, 1995

[54] ADJUSTABLE FACE SHIELD

[75] Inventors: Dennis L. Baker, Houlton, Wis.;
Susan A. Green, Shoreview, Minn.

[73] Assignee: Minnesota Mining and Manufacturing Company, St. Paul, Minn.

[21] Appl. No.: 143,833

[22] Filed: Oct. 27, 1993

[51] Int. Cl.⁶ .................... A61F 9/04; A62B 18/02
[52] U.S. Cl. ........................... 2/9; 2/173; 128/858; 128/206.17; 128/206.19
[58] Field of Search .............. 2/9, 173, 206, 174, 2/427; 128/206.19, 206.23, 201.17, 201.15, 201.12, 206.12, 206.21, 857, 858, 863

[56] References Cited

U.S. PATENT DOCUMENTS

| | | | |
|---|---|---|---|
| Re. 28,102 | 8/1974 | Mayhew | 128/146.2 |
| 450,515 | 4/1891 | Lamb . | |
| 1,800,051 | 4/1931 | Blanco | 2/206 |
| 1,923,340 | 8/1933 | Steckler | 2/174 |
| 2,029,947 | 2/1936 | Schmitt et al. | 128/146 |
| 2,056,753 | 10/1936 | Wagner | 128/141 |
| 2,149,067 | 2/1939 | Otero | 128/139 |
| 2,342,982 | 2/1944 | Stern et al. | 2/9 |
| 2,627,088 | 2/1953 | Alles et al. | 18/47.5 |
| 2,762,368 | 1/1956 | Bloomfield | 128/146 |
| 2,779,684 | 1/1957 | Alles | 117/7 |
| 3,017,888 | 1/1962 | Weiner | 128/400 |
| 3,792,702 | 2/1974 | Delest | 128/146.7 |
| 3,834,384 | 9/1974 | Raines | 128/146.2 |
| 4,419,993 | 12/1983 | Peterson | 128/201.15 |
| 4,642,267 | 2/1987 | Creasy et al. | 428/413 |
| 4,657,010 | 4/1987 | Wright | 128/205.25 |
| 4,796,621 | 1/1989 | Barle et al. | 128/206.23 |
| 4,797,956 | 1/1989 | Boyce | 2/431 |
| 4,821,340 | 4/1989 | Johnson | 2/9 |
| 4,825,878 | 5/1989 | Kuntz et al. | 128/857 |
| 4,920,960 | 5/1990 | Hubbard et al. | 128/206.12 |
| 4,944,294 | 7/1990 | Borek, Jr. | 128/206.19 |
| 4,969,457 | 11/1990 | Hubbard et al. | 128/206.12 |
| 5,020,533 | 6/1991 | Hubbard et al. | 128/206.23 |
| 5,067,174 | 11/1991 | Ritchey et al. | 128/201.17 X |
| 5,107,547 | 4/1992 | Scheu | 2/206 |
| 5,138,714 | 8/1992 | Smith | 2/9 |
| 5,150,703 | 9/1992 | Hubbard et al. | 128/206.12 |
| 5,303,423 | 4/1994 | Gazzara et al. | 128/857 X |

FOREIGN PATENT DOCUMENTS

| | | | |
|---|---|---|---|
| 0273040 | 9/1913 | Germany | 2/427 |
| WO89/10106 | 11/1989 | WIPO | A61F 9/04 |

*Primary Examiner*—Peter Nerbun
*Attorney, Agent, or Firm*—Gary L. Griswold; Walter N. Kirn; Jennie G. Boeder

[57] ABSTRACT

An adjustable face shield for protecting the face of the wearer, having a mask adapted to cover the nose and mouth of the wearer and a flexible eye shield having a transparent upper portion adapted to fit over the eyes of the wearer. The eye shield has a base portion fixedly attached to the mask so that the upper portion of the eye shield can pivot towards or away from the wearer's face. Adjustable attachment means mounted on the eye shield fits around the head of the wearer to position the eye shield over the eyes and is adapted to adjust the angular position of the upper portion of the eye shield relative to the face of the wearer as the adjustable means is moved up or down on the back of the head of the wearer.

11 Claims, 3 Drawing Sheets

ADJUSTABLE FACE SHIELD

TECHNICAL FIELD

This invention relates to a face shield having a face mask and an eye shield and having a means to adjust the eye shield for improved fit and comfort. The invention further relates to a method for providing the same.

BACKGROUND OF THE DISCLOSURE

Present face shields constructed by attaching transparent plastic film eye shields to face masks fit poorly and are uncomfortable. For example, a number of face shields have eye shield portions which fit close to the eyes and the nose of the wearer, but during use may form a scoop which allows potentially harmful liquid droplets (such as blood) to reach the wearer's eyes. Other eye shields fit so tightly that they can be uncomfortable. Wearers who must wear eye glasses have additional difficulties because the glasses hold the eye shield away from the face, thereby reducing the protection of the eyes from splashing liquids.

U.S. Pat. Nos. 4,797,956 to Boyce; 2,056,753 to Wagner; 4,796,621 to Barle et al; 4,825,878 to Kuntz et al; and 4,821,340 to Johnson disclose an eye shield of some sort worn in conjunction with a mask. In these references the eye shield is adapted to be worn in a certain position, fixed by an attachment at or above eye level in contact with or closely adjacent the wearer's face.

PCT Application PCT/US89/01629 to Russell discloses a face mask having an eye shield attached to its upper margin. An adjustable band may be included at the sides of the transparent eye shield portion to hold it in position over the eyes of the wearer. However, the eye shield is intended to be held in a fixed position close to the wearer's face with cushions to set off the eye shield from the face. U.S. Pat. No. 4,944,294 to Borek, Jr.; and 5,020,533 and 5,150,703 to Hubbard et al disclose face masks with visors or eye shields which attach to and extend upwards from masks, but where no means for pivoting the eye shields away from the face are disclosed.

SUMMARY OF THE INVENTION

The present invention ameliorates the limitations of the prior art by providing a face shield adapted for rapid and convenient adjustment of the position of the eye shield relative to the wearer's face. In broad terms the invention can be considered as an adjustable face shield for protecting the face of a wearer, having a mask adapted to cover the nose and mouth of the wearer;

an eye shield having an upper portion with at least a transparent section adapted to fit over the wearer's eyes and a base portion fixedly attached to the mask such that the upper portion can pivot towards or away from the wearer's face; and adjustable attachment means mounted on the eye shield for positioning the eye shield over the eyes of the wearer and adapted to adjust the angular position of the upper portion of the eye shield relative to the face of the wearer. In a first major embodiment, the adjustable attachment means includes a pair of tie straps having sufficient lengths to be tied around the head of the wearer, which tie straps are connected to the eye shield at connection locations on either side of the eye shield. The connection locations are positioned on each side of the eye shield such that moving the pair of joined ties to different places on the back of the wearer's head moves the eye shield to different angular positions relative to the face of the wearer. In a particularly preferred embodiment, the tie straps extend from opposite corners of the face mask and are connected to the eye shield by passing each tie strap through a hole located at the connection location on each side of the eye shield.

In a second major embodiment, the adjustable attachment means includes an elastic band adapted to fit over and around the head of the wearer. Each end of the elastic band is attached at opposite sides of the eye shield at connection locations which are positioned such that moving the elastic band to different places on the back of the wearer's head moves the eye shield to different angular positions relative to the face of the wearer.

The invention provides an adjustable face shield for protecting the face of a wearer, wherein the eye shield can be adjusted to various angular positions relative to the face of the wearer.

An advantage of the invention is that it allows the eye shield to be adjusted in such a way that the fit and comfort of the face shield are improved regardless of the wearer's facial shape or the presence of glasses.

Detailed Description of the Invention

Figure 1:
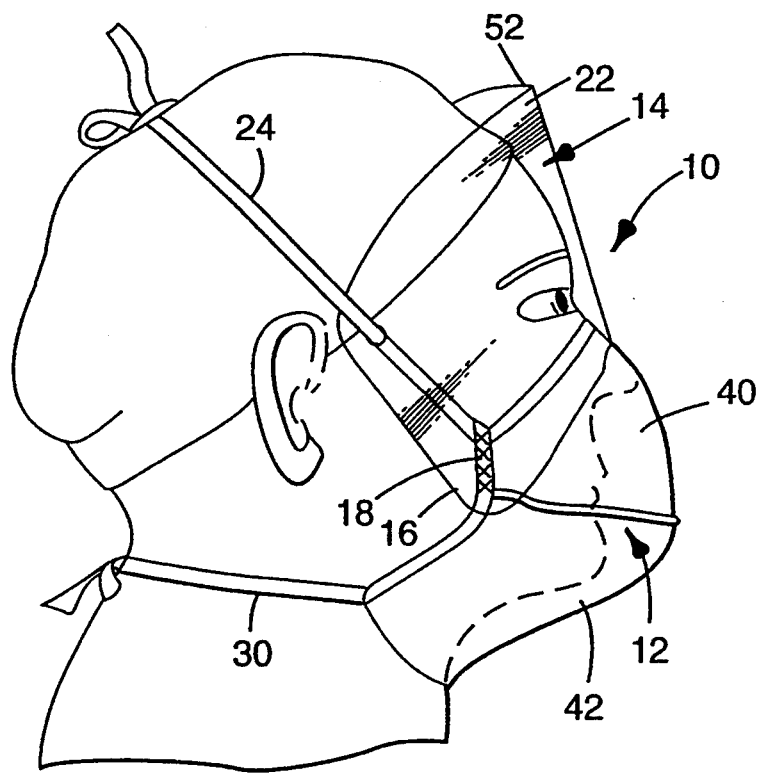
FIG. 1 is a side elevational view of a wearer fitted with a face shield constructed in accordance with the present invention, shown with adjustable attachment means positioned at a high point on the back of the wearer's head.
Figure 2:
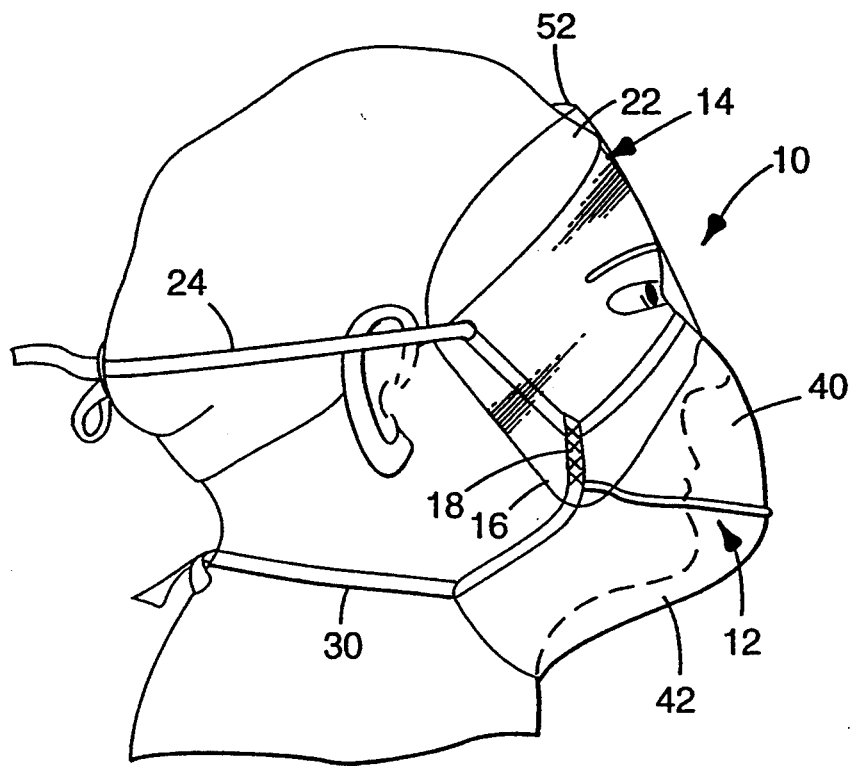
FIG. 2 is a side elevational view of a wearer fitted with the face shield of FIG. 1, shown with adjustable attachment means positioned at a low point on the back of the wearer's head.
Figure 3:
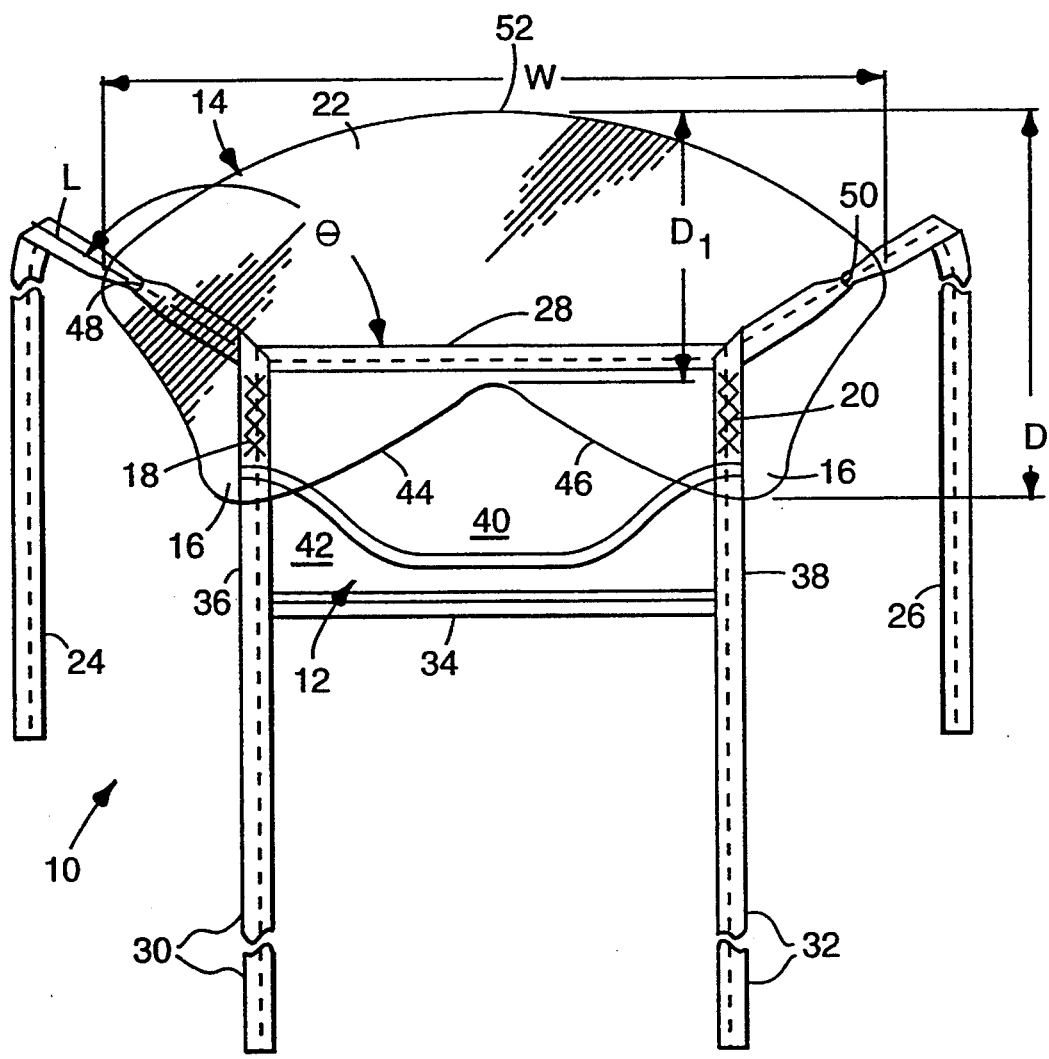
FIG. 3 is a front plan view of the face shield of FIG. 1.

Referring to FIGS. 1, 2 and 3, one embodiment of an adjustable face shield 10 is shown. In FIGS. 1, 2 and 3 like items are identified by like and corresponding numerals for ease of reference. A typical medical face mask 12 covers the nose, mouth and a portion of the chin of the wearer. An eye shield 14, having a base portion 16, bonded at bonding sites 18 and 20 to face mask 12, prevents liquids from splashing into the eyes of the wearer, while allowing clear vision to the wearer through transparent upper portion 22.

The face mask 12, which can be used in the face shield of the present invention, can be any of the commonly used face masks presently used by medical personnel. Typically, medical face masks are multi-layered constructions which allow the free passage of air but prevent the permeation of germs therethrough. Face mask 12 preferably is of the disposable anti-fogging "duckbill" type, fabricated in general as disclosed in U.S. Pat. No. 4,419,993, issued Dec. 13, 1983, and assigned to 3M, which patent is incorporated herein by reference. One or more ties or elastic bands extend from the side of the mask in order to secure the face mask to the face of the wearer. Alternative types of known surgical face masks disclosed in the following patents can also be utilized: U.S. Pat. Nos. 4,969,457; 4,944,294; 4,920,960; 3,834,384 ; and RE. 28,102 ; all of which are incorporated herein by reference. As illustrated in FIG. 3, in a preferred embodiment of the present invention the mask is of the "duckbill" type with an upper region 40 having a permeability which differs from the lower region 42 (as discussed in U.S. Pat. No. 4,419,993) to provide anti-fogging properties. The mask 12 has an upper edge 28, a lower edge 34, and two opposing side edges 36 and 38.

A first pair of complementary tie strings or straps 24 and 26 extend from the opposing sides of the upper edge 28 of the mask 12 to form adjustable attachment means. The face shield is customarily positioned over the eyes of the wearer by tying the straps 24 and 26 into a knot behind the wearer's head. A second pair of tie straps 30 and 32 extending from the opposing sides of the lower edge 34 of the mask 12 form a second attachment means which are similarly tied behind the wearer's neck, in order to cover the nose and mouth of the wearer. The straps 24, 26, 30 and 32 may either be separately fastened to the far corners of the face mask, or (as shown in FIG. 3) straps 24 and 30 and straps 26 and 32 are integrated pieces of binding strips forming side edges 36 and 38 of the face mask.

Eye shield 14 is preferably made entirely of a clear thermoplastic or thermoset film. Useful materials include polyester, such as polyethylene terephthalate (PET), polystyrene-co-polyacrylonitrile, polyolefins, such as polyethylene or their copolymers, polycarbonate, polyacrylates, such as polymethyl methacrylate, polyethyl acrylate or their copolymers, polysulfone, polyvinylidene chloride or polyvinylidene fluoride, and cellulosics such as cellulose acetate butyrate. Most preferably eye shield 14 is made of polyethylene terephthalate or polyethylene. The thermoplastic eye shield is preferably flexible enough to conform to the contours of the face of the wearer, yet stiff enough to hold a form without collapsing. To provide this degree of flexibility, the thermoplastic material is generally about 0.3 to 0.05 mm thick, most preferably about 0.1 mm thick. Preferably, the thermoplastic film is coated with an anti-fogging agent to prevent fogging caused by the condensation of moisture exhaled by the wearer. Suitable anti-fogging treatments include those disclosed in U.S. Pat. Nos. 2,627,088; 2,779,684 ; and 4,642,267 all incorporated herein by reference. Useful anti-fogging and anti-reflective treatments include those disclosed in U.S. Ser. Nos. 07/957,217 and 07/957,235, both incorporated herein by reference.

Eye shield 14 is generally dimensioned to generously fit across the width of face mask 12, becoming wider as it extends over the forehead of the wearer. Preferably, in order to accommodate the nose, the center of the bottom of eye shield 14 has a concave cut out bounded by arcuate edges 44 and 46 as shown in FIG. 3. The cut out portion is designed to assist the eye shield 14 to bend around the nose of the wearer without creasing as shown in FIG. 3. In a preferred embodiment, the depth D of the eye shield 14 is about 12 cm, the depth at the center of the eye shield, D1, is about 10 cm, and the width W at the widest part of the eye shield is about 30 cm.

Eye shield 14 is affixed to opposite upper side edges of mask 12 at bonding sites 18 and 20 by means such as adhesives, ultrasonic or induction welding, thermal bonding or mechanical fastening means. Useful adhesive means include transfer or hot melt adhesives, or double sided tape. Useful mechanical means include staples, mechanical fasteners such as snaps or hook and loop, or sewing. Eye shield 14 is preferably affixed to mask 12 by adhesives or double sided tape. Bond sites 18 and 20 are preferably only of sufficient area (approximately 1.0 cm wide by 2.6 cm long) to secure the eye shield 14 to the mask 12. While not essential to the operation of the face shield, it has been found that the eye shield 14 more easily adapts to the contours of the face of the wearer if the bonding sites 18 and 20 do not extend across the entire upper edge 28 of the mask. Eye shield 14 is preferably placed in an overlapping relationship so that approximately 40% of its depth (D) covers mask 12. This provides sufficient overlap at the center of face shield be to prevent gaps when adjustments are made for comfort and fit. Alternatively, the face mask could overlay the eye shield. Upper portion 22 of the eye shield has holes 48 and 50 at opposite sides of the eye shield. Holes 48 and 50 are positioned on a line L which forms an obtuse angle, $\ominus$, of about 135 to 165 degrees with the upper edge 28 of the face mask. Alternatively, line L forms the obtuse angle with a line running between points on each bonding site 18 and 20 which are closest to the upper edge 28 of the face mask. Preferably, angle $\ominus$ is about 145 to 155 degrees, more preferably about 150 degrees. Preferably, holes 48 and 50 are located along line L a distance of at least about 2 cm from bonding sites 18 and 20, more preferably about 2 to 7 cm and most preferably about 5.1 cm from the vertex of angle $\ominus$.

Tie straps 24 and 26 are inserted through holes 48 and 50, respectively, from the internal surface of the eye shield. Tie straps 24, 26, 30 and 32 may be composed of polyester, polyethylene, nylon, other plastics, rayon, cotton, reinforced paper, or combinations thereof. Once inserted through the holes 48 and 50, the tie straps 24 and 26 lie on the external surface of the eye shield. When the tie straps 24 and 26 are joined at the back of the head of the wearer, holes 48 and 50 act as pivotal points for the upper portion 22 of the eye shield. By moving the joined tie straps 24 and 26 downwardly or upwardly on the back of the head of the wearer, the upper portion 22 of the eye shield can be adjusted from just touching the face of the wearer to a distance of several centimeters away from the face. Referring to FIG. 2, as the tie straps 24 and 26 are moved down along the back of the head of the wearer, towards the neck, the upper portion 22 of the eye shield pivots at bonding sites 18 and 20 and moves closer to the face of the wearer. Referring to FIG. 1, as the tie straps 24 and 26 are moved up along the back of the head towards the crown of the head, the upper portion 22 of the eye shield pivots at bonding sites 18 and 20 and moves away from the face of the wearer. Preferably, the plane of the eye shield rotates at least about 10 degrees, more preferably about 20 degrees as the tie straps are adjusted upwardly or downwardly on the back of the head. For optimal results the plane of the eye shield should rotate no more than about 30 degrees as the position of the tie straps is adjusted. For example, as best illustrated by FIGS. 1 and 2, where the distance between each of the holes 48 and 50, and bonding sites 18 and 20 is about 5.1 cm and $\ominus$ is about 150 degrees, an approximately 30 degree rotation of the tie straps 24 and 26 about bonding sites 18 and 20, respectively, (by moving the tie straps 24 and 26 up or down on the back of the head) produces a movement of the center top edge 52 of the eye shield of about 5.1 cm. Movement of the eye shield will, however, vary depending upon the face shape of the wearer and the tightness of tie straps 24 and 26. Thus, the wearer, by moving tie straps 24 and 26, can position the eye shield to provide maximum protection, comfort and fit.

Figure 4:
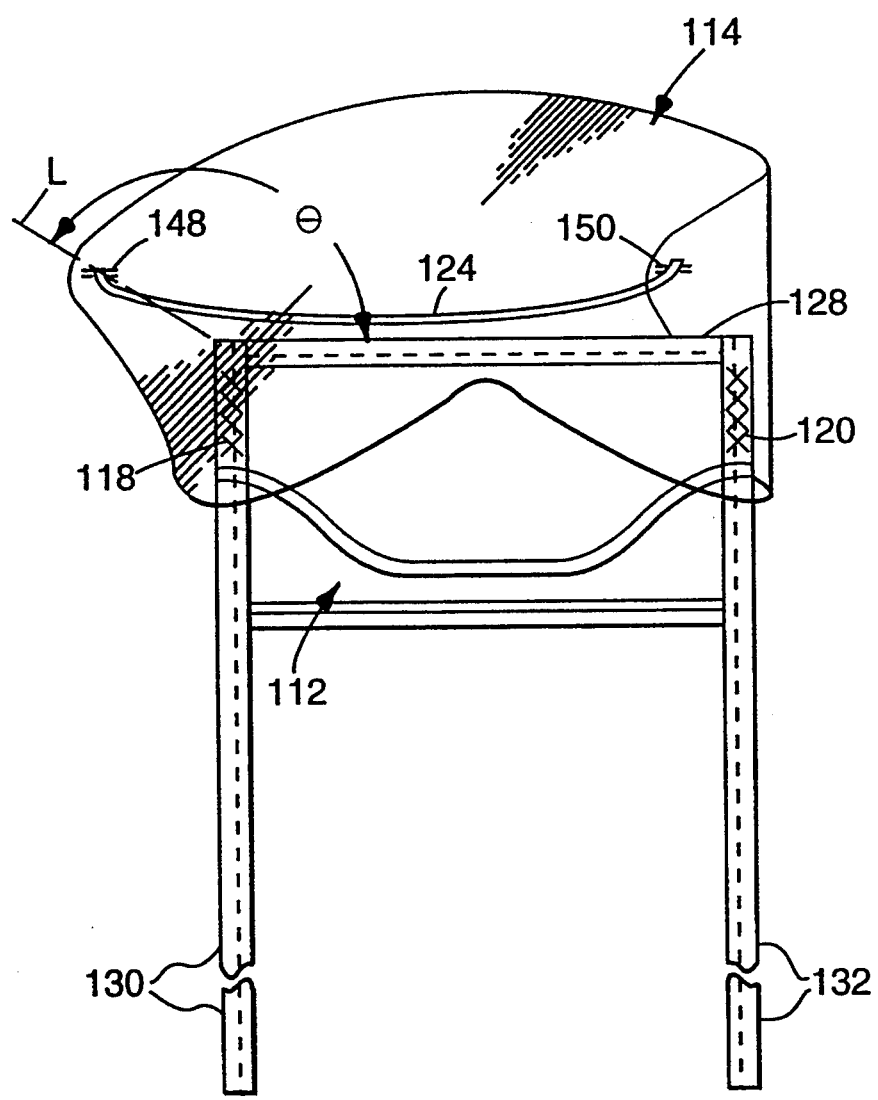
FIG. 4 is a front plan view of an alternate embodiment of the face shield of the present invention.

Referring to FIG. 4, an alternate embodiment of the present invention is to substitute an elastic band 124 for tie straps 24 and 26. Elastic band 124 is attached to opposite sides of the eye shield 114 at connection locations 148 and 150. Like holes 48 and 50 in the embodiment depicted in FIG. 3, connection locations 148 and 150 are positioned on a line L which forms an obtuse angle $\ominus$ of about 135 to 165 degrees with the upper edge 128 of the face mask. Preferably, angle $\ominus$ is about 145 to 155 degrees, more preferably about 150 degrees. Preferably, connection locations 148 and 150 lie along line L a distance of at least about 2 cm, more preferably about 2 to 7 cm, and most preferably about 5.1 cm from the vertex of angle $\ominus$.

Elastic band 124 may be natural rubber or a synthetic elastomer such as polyisoprene, poly-butadiene, copolymers of a diene and styrene, copolymers of acrylonitrile and a diene, polychloroprene, copolymers of chloroprene and other monomers, ethylene propylene elastomers including ethylene propylene copolymers and ethylene propylene diene terpolymers, and thermoplastic elastomers which are block copolymers of styrene and butadiene or isoprene. Elastic band 124 may also contain a polyurethane fiber. Natural rubber is the preferred elastic component in band 124.

In a fashion analogous to that in the embodiment depicted in FIG. 3, movement of elastic band 124 to different positions on the back of the wearer's head allows the wearer to adjust the distance between his face and eye shield 114.

Another embodiment of the present invention (not shown) is to substitute other adjustable attachment means, such as hook and loop fasteners, for the elastic band 124 or the tie straps 24 and 26 either entirely or in part.

As various changes could be made in the above constructions and methods without departing from the scope of the invention, it is intended that all matter contained in the above description be interpreted as illustrative and not in a limiting sense.

We claim:

1. An adjustable face shield for protecting the face of a wearer, comprising:
    a mask adapted to cover the nose and mouth of the wearer, said mask having an upper edge, a lower edge, and two opposing side portions adapted to be on either side of the wearer's face;
    an eye shield having an upper portion with at least a transparent section adapted to fit over the wearer's eyes, two opposing side portions adapted to be on either side of the wearer's face and a base portion, said base portion of the eye shield being fixedly attached to the mask such that said upper portion can pivot towards or away from the wearer's face;
    adjustable attachment means for positioning the eye shield over the eyes of the wearer, the adjustable attachment means connected to the upper portion of the eye shield at at least one connection location on each side portion of the eye shield, each connection location lying on a line which forms an obtuse angle of approximately 135 to 165 degrees with the upper edge of the face mask, and each connection location being at least about 2 cm from the upper edge of the face mask.

2. An adjustable face shield according to claim 1 wherein the adjustable means is adapted to fit around the head of the wearer and is positioned such that the upper portion of the eye shield will move away from the face of the wearer as the adjustable means is moved up along the back of the head towards the crown of the head, and the upper portion of the eye shield will move closer to the face of the wearer as the adjustable means is moved down the back of the head towards the neck of the wearer.

3. An adjustable face shield according to claim 1 wherein the adjustable means is adapted such that the angular position of the upper portion of the eye shield may be rotated at least 10 degrees.

4. An adjustable face shield according to claim 1 wherein the angle between the line and the upper edge of the face mask is approximately 150 degrees.

5. An adjustable face shield according to claim 1 wherein said mask further comprises a second attachment means extending from the lower edge of the mask for removably attaching the mask over the nose and mouth of the wearer, said adjustable attachment means and said second attachment means each comprising a pair of ties having sufficient lengths to be tied around the head and neck, respectively, of the wearer.

6. An adjustable face shield according to claim 1 wherein said adjustable attachment means comprises an elastic band adapted to fit over and around the head of the wearer.

7. An adjustable face shield according to claim 1 wherein the adjustable attachment means are mechanically or adhesively affixed to the eye shield at the connection locations.

8. An adjustable face shield according to claim 1 wherein the eye shield is fixedly attached to the mask at the bonding sites located at least partially at the side portions of the mask by mechanical or adhesive means.

9. An adjustable face shield according to claim 1 wherein the eye shield has a concave cut-out portion in the center of the base portion adapted to conform the face shield to the face of the wearer.

10. An adjustable face shield for protecting the face of a wearer, comprising:
    a mask adapted to cover the nose and mouth of the wearer, said mask having an upper edge, a lower edge, two opposing side portions adapted to be on either side of the wearer's face and two opposing side edges, one at each side portion of the mask, the side edges separating the upper and lower edges of the mask;
    an eye shield having an upper portion with at least a transparent section adapted to fit over the wearer's eyes, two opposing side portions adapted to be on either side of the wearer's face and a base portion overlying at least the upper edge of the mask, said base portion of the eye shield being fixedly attached to the mask at bonding sites located at least partially at the side portions of the mask;
    a first pair of ties having sufficient lengths to be tied around the head and neck, respectively, of the wearer, each tie extending from the point of the face mask at which the side edges of the mask intersect the upper edge of the mask and connecting to the side portion of the eye shield by passing through a hole in the eye shield, each hole being located on a line which forms an obtuse angle of approximately 135 to 165 degrees with the upper edge of the face mask;

a second pair of ties extending from each side of the lower edge of the mask and having sufficient lengths to be tied around the head and neck, respectively, of the wearer.

11. A method of making an adjustable face shield for protecting the face of a wearer comprising:

joining an eye shield to a mask adapted to cover the nose and mouth of the wearer, said eye shield having an upper portion with at least a transparent section adapted to fit over the wearer's eyes, two opposing side portions adapted to be on either side of the wearer's face and a base portion, said base portion of the eye shield being fixedly attached to the mask such that said upper portion can pivot towards or away from the wearer's face; and providing adjustable attachment means for positioning the eye shield over the eyes of the wearer, by connecting such adjustable attachment means to the upper portion of the eye shield at at least one connection location on each side portion of the eye shield, each connection location positioned to lie on a line which forms an obtuse angle of approximately 135 to 165 degrees with the upper edge of the face mask, and each connection location being at least about 2 cm from the upper edge of the face mask.

* * * * *